(12) United States Patent
Andersen et al.

(10) Patent No.: US 10,881,864 B2
(45) Date of Patent: Jan. 5, 2021

(54) METHODS AND SYSTEMS FOR GENERATING STIMULATION WAVEFORMS FOR A NEUROSTIMULATION THERAPY

(71) Applicant: PACESETTER, INC., Sylmar, CA (US)

(72) Inventors: Dean Andersen, San Jose, CA (US); Gavin Rade, Dallas, TX (US)

(73) Assignee: PACESETTER, INC., Sylmar, CA (US)

( * ) Notice: Subject to any disclaimer, the term of this patent is extended or adjusted under 35 U.S.C. 154(b) by 246 days.

(21) Appl. No.: 15/702,447

(22) Filed: Sep. 12, 2017

(65) Prior Publication Data
US 2019/0076663 A1    Mar. 14, 2019

(51) Int. Cl.
| | | |
|---|---|---|
| A61N 1/37 | (2006.01) | |
| A61N 1/372 | (2006.01) | |
| A61N 1/36 | (2006.01) | |
| A61N 1/05 | (2006.01) | |

(52) U.S. Cl.
CPC ..... *A61N 1/37247* (2013.01); *A61N 1/36125* (2013.01); *A61N 1/36167* (2013.01); *A61N 1/0553* (2013.01); *A61N 1/37223* (2013.01)

(58) Field of Classification Search
USPC .............................................. 607/58, 60–61
See application file for complete search history.

(56) References Cited

U.S. PATENT DOCUMENTS

| | | | | |
|---|---|---|---|---|
| 5,370,672 A | * | 12/1994 | Fowler | A61N 1/32 607/58 |
| 2006/0259098 A1 | * | 11/2006 | Erickson | A61N 1/3787 607/61 |

* cited by examiner

*Primary Examiner* — Nicole F Lavert
(74) *Attorney, Agent, or Firm* — The Small Patent Law Group LLC; Dean D. Small

(57) ABSTRACT

The methods and systems herein generally relate to generating stimulation waveforms for a therapy of a neurostimulation (NS) device in a patient. The methods and systems receive a target stimulation waveform from a user interface, calculate a timing resolution of the target stimulation waveform, determine target amplitude resolutions of the target stimulation waveform, identify whether a mathematical relationship exists between the target amplitude resolutions, and automatically designate one of a first, second, or third generator circuits based on at least one of the timing resolution, the amplitude, or the mathematical relationship. The systems and methods further transmit the target stimulation waveform and an activation instruction for the designated one of the first, second, or third generator circuits along the communication link to a NS device. The NS device includes the first, second, and third generator circuits configured to generate different first, second, and third types of stimulation waveforms.

7 Claims, 7 Drawing Sheets

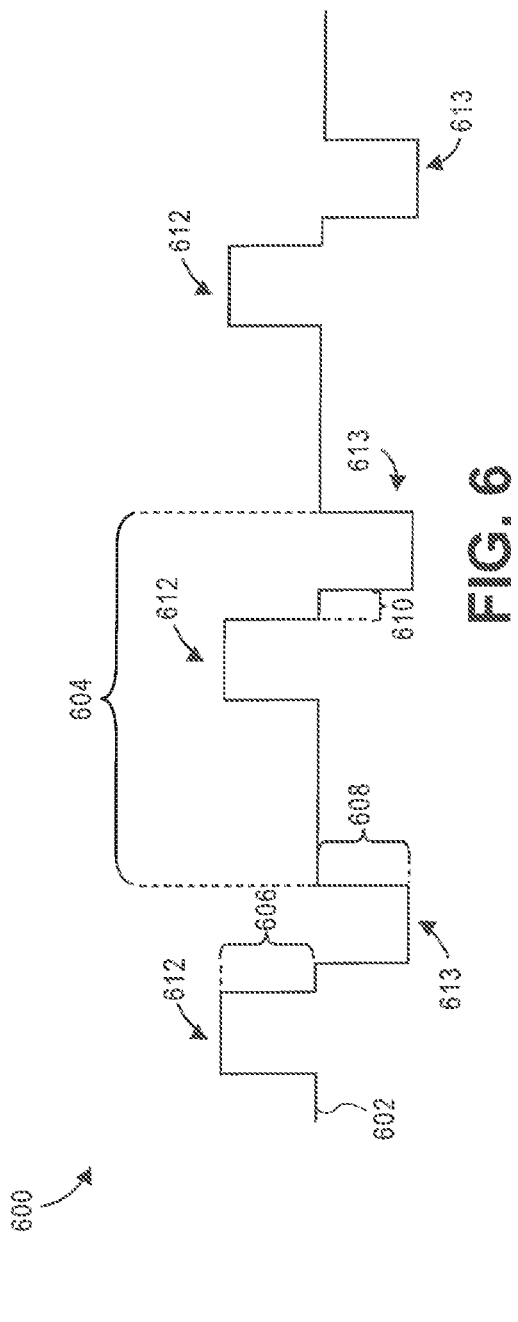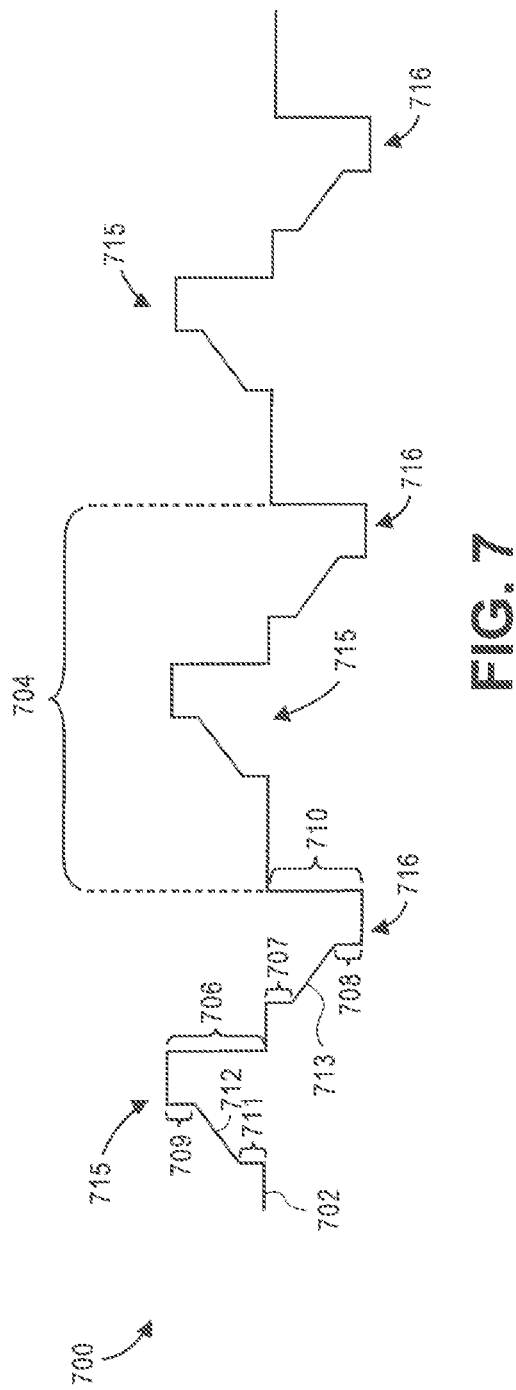

METHODS AND SYSTEMS FOR GENERATING STIMULATION WAVEFORMS FOR A NEUROSTIMULATION THERAPY

BACKGROUND OF THE INVENTION

Embodiments herein generally relate to generating stimulation waveforms for a therapy of a neurostimulation (NS) device in a patient.

Conventional NS devices are devices that generate electrical pulses and deliver the pulses to neural tissue to treat a variety of disorders. NS devices may be used to manage one or more conditions of a patient by delivering NS therapy. The NS devices can include deep brain stimulation, tremors, dystonia, spinal cord stimulation, dorsal root ganglion stimulation, peripheral nerve stimulation, and/or the like. The NS therapy is delivered by the NS device as electrical impulses through electrodes implanted in the one or more target regions of the nervous system. The electrical impulses are configured by a clinician based on one or more stimulation parameters (e.g., an intensity, a frequency, a pulse width, a duty cycle, an NS therapy type).

The NS therapy delivered by the NS devices are generated by dedicated hardware circuits, such as contained within an application specific integrated circuit. The most general form of dedicated hardware generates NS therapy as rectangular pulse trains of either constant voltage or constant current. For example, to form non-rectangular pulse trains (e.g., triangular waves, sine waves, sawtooth waves) the NS device may use additional hardware or software running on a microprocessor to adjust the rectangular pulses dynamically. However, the use of additional hardware or software resources requires additional power from a power source of the NS device, which reduces an operating life of the NS device.

A need remains for improved methods and systems for generating NS therapy.

SUMMARY

In accordance with an embodiment, a system (e.g., for generating a stimulation waveform for a neurostimulation therapy) is provided. The system includes a user interface configured to receive a user input indicative of a target stimulation waveform, and a communication circuit. The communication circuit is configured to establish a communication link with a neurostimulation (NS) device that includes first, second, and third generator circuits. The first, second, and third generator circuits are configured to generate different first, second, and third types of stimulation waveforms, such that the first, second, and third generating circuit generate varying degrees of stimulation waveform complexity. The system includes a controller circuit operably coupled to the user interface and the communication circuit. The controller circuit is configured to calculate a timing resolution of the target stimulation waveform, determine target amplitude resolutions of the target stimulation waveform, identify whether a mathematical relationship exists between the target amplitude resolutions, and automatically designate one of the first, second, or third generator circuits based on at least one of the timing resolution, the target amplitude resolutions, or the mathematical relationship between the target amplitude resolutions. The controller circuit is configured to transmit the target stimulation waveform and an activation instruction for the designated one of the first, second, or third generator circuits along the communication link.

Optionally, the controller circuit is configured to compare the timing resolution with a clock timing resolution for a clock of the first generator circuit. The clock timing resolution defining a frequency limit of the first type of stimulation waveform. The controller circuit automatically selects the first generator circuit when the timing resolution falls within the clock timing resolution.

Optionally, the controller circuit is configured to compare the target amplitude resolutions with a supported amplitude of the first generator circuit. The controller circuit automatically designates the first generator circuit when the target amplitude resolutions fall within the supported amplitude.

Optionally, the activation instruction activates the first generator circuit. The first generator circuit includes a counter and a comparator that are configured to activate individual switches of an array of switches to generate the first type of stimulation waveform.

Optionally, the controller circuit is configured to automatically designate the second generator circuit when no mathematical relationship exists between the target amplitude resolutions, and the timing resolution differs from a clock timing resolution for a clock of the first generator circuit.

Optionally, the activation instruction activates the second generator circuit. The second generator circuit includes a tangible and non-transitory memory that is configured to activate individual switches of an array of switches to generate the second type of stimulation waveform. For example, the controller circuit is configured to select the second generator circuit if the timing resolution and/or the amplitude resolutions are not within the capabilities of the first generator. The targeted stimulation waveform can be within the timing resolution and/or the amplitude resolutions of the second generator circuit. The second generator circuit having a higher timing resolution relative to the first generator circuit.

Optionally, the controller circuit is configured to automatically designate the third generator circuit when the mathematical relationship exists. For example, the mathematical relationship between the target amplitude resolutions can be described and/or represented as a set of instructions.

Optionally, the activation instruction activates the third generator circuit. The third generator circuit includes one or more processors configured to execute programmed instructions stored on a tangible and non-transitory memory, which activates individual switches of an array of switches to generate the third type of stimulation waveform.

In accordance with an embodiment, a method (e.g., for generating a stimulation waveform for a neurostimulation therapy) is provided. The method includes receiving a target stimulation waveform from a user interface, calculating a timing resolution of the target stimulation waveform, determining a target amplitude resolutions of the target stimulation waveform, identifying whether a mathematical relationship exists between the target amplitude resolutions, and automatically designating one of a first, second, or third generator circuits based on at least one of the timing resolution, the target amplitude resolutions, or the mathematical relationship. The method includes transmitting the target stimulation waveform and an activation instruction for the designated one of the first, second, or third generator circuits along the communication link to a neurostimulation (NS) device. The NS device includes the first, second, and third generator circuits configured to generate different first, second, and third types of stimulation waveforms.

Optionally, the method includes comparing the timing resolution with a clock timing resolution for a clock of the first generator circuit. The clock timing resolution defines a frequency limit of the first type of stimulation waveform. The first generator circuit is automatically designated when the timing resolution falls within the clock timing resolution.

Optionally, the method includes comparing the target amplitude resolutions with a supported amplitude of the first generator circuit. The first generator circuit is automatically designated when the target amplitude resolutions fall within the supported amplitude.

Optionally, the activation instruction activates the first generator circuit. The first generator circuit includes a counter and a comparator that are configured to activate individual switches of an array of switches to generate the first type of stimulation waveform.

Optionally, the automatically designating operation of the method includes designating the second generator circuit when no mathematical relationship exists between the target amplitude resolutions, and the timing resolution differs from a clock timing resolution for a clock of the first generator circuit, and is within a timing resolution of the second generator circuit.

Optionally, the activation instruction activates the second generator circuit that includes a tangible and non-transitory memory that is configured to activate individual switches of the array of switches to generate the second type of stimulation waveform.

Optionally, the automatically designating operation of the method includes designating the third generator circuit when the mathematical relationship exists.

Optionally, the activation instruction activates the third generator circuit that includes one or more processors that is configured to execute programmed instructions stored on a tangible and non-transitory memory, which is configured to activate individual switches of the array of switches to generate the second type of stimulation waveform.

Optionally, the activation instruction includes instructing the first, second, or third generator circuits that are not automatically designated to enter a sleep mode.

In accordance with an embodiment, a neurostimulation NS device (e.g., for generating a stimulation waveform) is provided. The NS device includes a communication circuit configured to establish a communication link with an external device, and a multiplexer operatively coupled to an array of switches and first, second, and third generator circuits. The array of switches are operably coupled to an electrical source circuit and a timer circuit. The NS device includes the first generator circuit having a counter and a comparator configured to activate individual switches of the array of switches based on a clock timing resolution for a clock representing a first type of stimulation waveform. The NS device includes the second generator circuit having one or more processors configured to execute programmed instructions stored on a first tangible and non-transitory memory configured to activate individual switches of the array of switches representing a second type of stimulation waveform. The NS device includes the third generator circuit having a second tangible and non-transitory memory that is configured to activate individual switches of the array of switches based on a third type of stimulation waveform.

Optionally, the communication circuit receives the target stimulation waveform, and an activation instruction to activate one of the first, second, or third generator circuits along the communication link. Additionally or alternatively, the activation instruction includes instructions for the first, second, or third generator circuits that are not activated to enter a sleep mode.

BRIEF DESCRIPTION OF THE DRAWINGS

FIG. 6 is a graphical illustration of an embodiment of a target stimulation waveform.

FIG. 7 is a graphical illustration of an embodiment of a target stimulation waveform.

DETAILED DESCRIPTION

Figure 1:
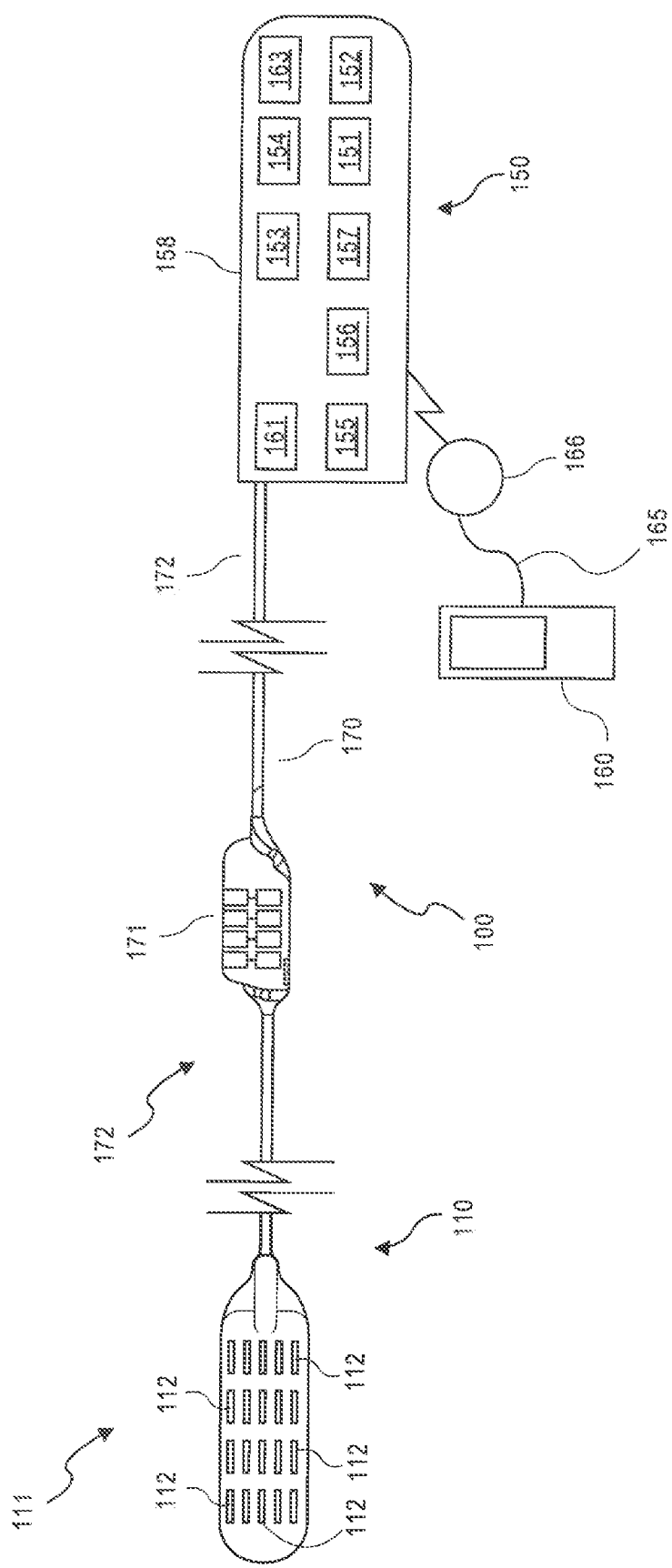
FIG. 1 depicts a schematic block diagram of an embodiment of a neurostimulation device.
Figure 2A:
FIGS. 2A-2I respectively depict stimulation portions of embodiments for inclusion at the distal end of a lead.
Figure 2B:
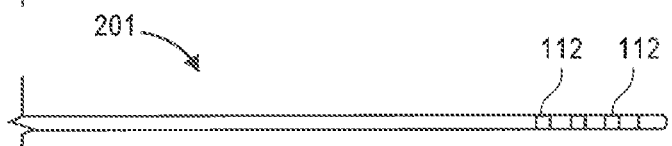
Figure 2C:
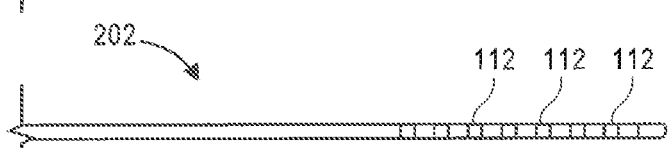
Figure 2D:
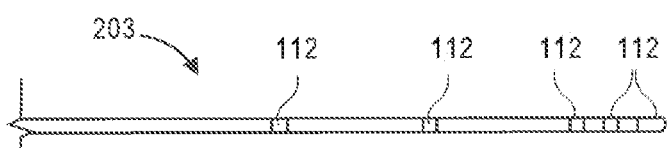
Figure 2E:
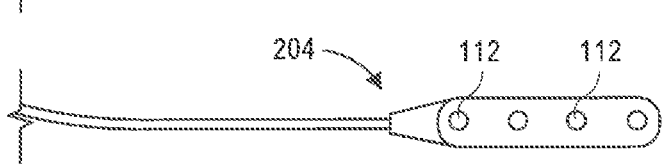
Figure 2F:
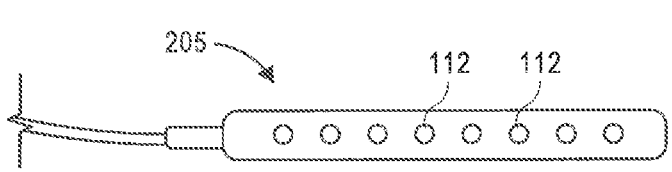
Figure 2G:
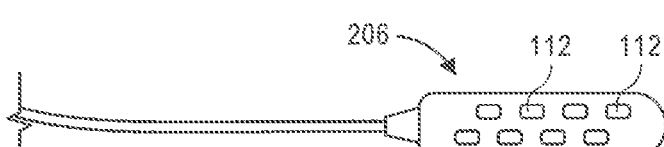
Figure 2H:
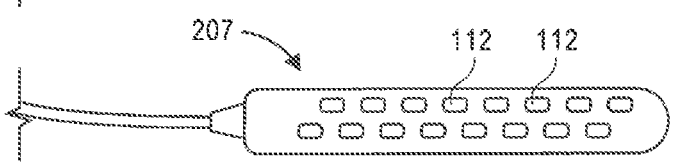
Figure 2I:
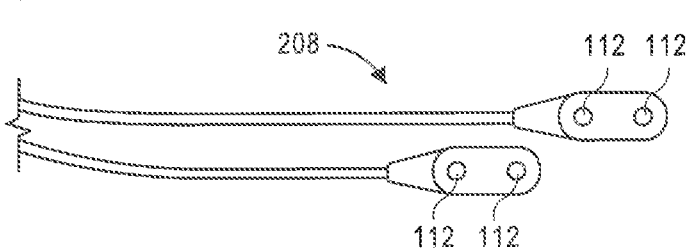

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Terms

The term "supported amplitudes" refers to a range or maximum, amplitude that can be generated by a waveform generator circuit. The supported amplitudes can represent a series discrete amplitudes that the waveform generator circuit can output. Additionally or alternatively, the supported amplitudes can be a continuous range of amplitudes.

The term "mathematical relationship" refers to an algorithm, formula, or a pattern that defines a shape (e.g., amplitude, pulse widths, pulse repetition frequency) of the waveform. Non-limiting examples of a mathematical relationship includes a sinusoidal relationship (e.g., oscillation) of the target amplitude resolutions, pseudo-random target amplitude resolutions overtime, a dependency of the target amplitude resolutions, an exponential relationship of the target amplitude resolutions, a parabolic relationship of the target amplitude resolutions, and/or the like.

The term "type of stimulation waveform" refers to a group or class of stimulation waveforms having one or more common characteristics that enable the stimulation waveforms within the group or class to be generated by a type of generator circuit.

For example, a "first type of stimulation waveform" includes one or more pulses having a fixed shape (e.g., rectangular pulses). The one or more pulses have common repeating target amplitude resolutions, and pulse widths. The target amplitude resolutions of the one or more pulses are limited by a supported amplitude of a hardware circuit based generator also referred to as a first generator circuit. The pulse widths of the one or more pulses are limited by a clock timing resolution of the first generator circuit. The clock timing resolution represents a frequency limit of the first generator circuit. The clock timing resolution represents a minimum pulse width and/or frequency of the first stimulation waveform.

For example, a "second type of stimulation waveform" includes one or more pulses generated by a direct memory access (DMA) based generator, also referred to as a second generator circuit. The one or more pulses can include rectangular pulses or non-rectangular pulses. Non-limiting examples of the non-rectangular pulses include triangle pulses, sawtooth pulses, and/or the like. The one or more pulses have a target amplitude resolutions. No mathematical relationship exists between the target amplitude resolutions of the one or more pulses.

For example, a "third type of stimulation waveform" includes one or more pulses generated by a processor based generator, also referred to as a third generator circuit. The one or more pulses can include rectangular pulses or non-rectangular pulses. The one or more pulses have target amplitude resolutions. A mathematical relationship exists between the target amplitude resolutions of the one or more pulses, which form the third type of stimulation waveform.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Embodiments herein describe an external device configured to automatically manage operation of an NS device that include a first, second, or third generator circuits. The first, second, and third generator circuits are configured to generate different first, second, and third types of stimulation waveforms, respectively. The NS device is versatile as it includes the first, second, and third generator circuits that have different flexibility and power trade-offs.

The first generator circuit represents dedicated hardware configured to generate pulses with a fixed shape (e.g., rectangular pulses). The first generator circuit has a higher power efficiency relative to the second and third generator circuits. Based on the dedicated hardware, the degree to which the first type of stimulation waveform can be varied is limited. For example, the first type of stimulation waveform is limited by a clock timing resolution and one or more supported amplitudes of rectangular pulses of the first generator circuit. For example, the first generator circuit may only generate stimulation waveforms that have a limited number of pulse amplitudes and/or limited number of frequencies. The second generator circuit represents a tangible and non-transitory memory having data representing different states to form the second type of stimulation waveform. For example, the second generator circuit has more flexibility relative to the first generator circuit. The second generator circuit is not limited by a clock timing resolution as the first generator circuit and/or the one or more supported amplitudes. The second generator circuit requires memory resources and is less power efficient relative to the first generator circuit. The third generator circuit includes one or more processors configured to execute programmed instructions on a tangible and non-transitory memory. The third generator circuit executes algorithms representing a mathematical relationship between amplitudes to form the third stimulation waveform. The third generator circuit is the least power efficient relative to the first and second generator circuits.

In accordance with embodiments, the external device receives the target stimulation waveform from a clinician (e.g., doctor, nurse, patient) via a user interface. The external device identifies characteristics of the target stimulation waveform, such as a timing resolution, target amplitude resolutions, and a mathematical relationship between the target amplitude resolutions. The timing resolution represents a pulse width and/or repetition rate of the target stimulation waveform. The target amplitude resolutions represent a current and/or voltage amplitude of pulses of the target stimulation waveform, which may be the same and/or different with respect to each other. The mathematical relationship is indicative of a pattern between the amplitudes of the target stimulation waveform, which can be represented as an algorithm. For example, the mathematical relationship may represent a sinusoidal relationship (e.g., oscillation) of the amplitudes, pseudo-random amplitudes overtime, a dependency of the amplitudes, exponential relationship of the amplitudes, parabolic relationship of the amplitudes, and/or the like. Based on the characteristics of the target stimulation waveform, the external device designates one of the first, second, or third generator circuits to generate the target stimulation waveform that is the most efficient (e.g., power efficiency). For example, the external device designates the first, second, or third generator circuits based on matching the first, second, and third types of stimulation waveforms with the characteristics of the target stimulation waveform.

FIG. 1 depicts a schematic block diagram of an embodiment of a neurostimulation (NS) device 100. The NS device 100 is configured to generate electrical pulses (e.g., excitation pulses) for application to tissue of a patient according to one embodiment. For example, the NS device 100 may be adapted to stimulate spinal cord tissue, dorsal root, dorsal root ganglion, peripheral neural tissue, deep brain tissue, cortical tissue, cardiac tissue, digestive tissue, pelvic floor tissue, and/or any other suitable neural tissue of interest within a patient's body.

The NS device 100 includes an implantable pulse generator (IPG) 150 that is adapted to generate electrical pulses for application to neural tissue of a patient. The IPG 150 typically comprises a metallic housing 158 that encloses a first generating circuit 152, a second generating circuit 163, a third generating circuit 151, a charging coil 153, a battery 154, a communication circuit 155, battery charging circuitry 156, switching circuitry 157, a memory 161, and/or the like. The communication circuit 155 may represent hardware that is used to transmit and/or receive data along a uni-directional or a bi-directional communication link (e.g., with an external device 160).

The IPG 150 may include a separate or an attached extension component 170. The extension component 170 may be a separate component. For example, the extension component 170 may connect with a "header" portion of the IPG 150, as is known in the art. If the extension component 170 is integrated with the IPG 150, internal electrical connections may be made through respective conductive components. Within the IPG 150, electrical pulses are generated by the first, second, or third generating circuits 152, 163, 151 and are provided to the switching circuitry 157. The switching circuitry 157 connects to outputs of the IPG 150. Electrical connectors (e.g., "Bal-Seal" connectors)

within the connector portion 171 of the extension component 170 or within the IPG header may be employed to conduct various stimulation pulses. The terminals of one or more leads 110 are inserted within the connector portion 171 or within the IPG header for electrical connection with respective connectors. The pulses originating from the IPG 150 are provided to the one or more leads 110. The pulses are then conducted through the conductors of the lead 110 and applied to tissue of a patient via an electrode array 111. Any suitable known or later developed design may be employed for connector portion 171.

The electrode array 111 may be positioned on a paddle structure of the lead 110. For example, in a planar formation on a paddle structure as disclosed in U.S. Provisional Application No. 61/791,288, entitled, "PADDLE LEADS FOR NEUROSTIMULATION AND METHOD OF DELIVERING THE SAME," which is expressly incorporated herein by reference. The electrode array 111 includes a plurality of electrodes 112 aligned along corresponding rows and columns. Each of the electrodes 112 are separated by non-conducting portions of the paddle structure, which electrically isolate each electrode 112 from an adjacent electrode 112. The non-conducting portions may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethytene (PTFE) (e.g., Teflon), or parylene coating, polyether bloc amides, polyurethane. The electrodes 112 may be configured to emit pulses in an outward direction.

Optionally, the IPG 150 may have one or more leads 110 connected via the connector portion 171 of the extension component 120 or within the IPG header. For example, a DRG stimulator, a steerable percutaneous lead, and/or the like. Additionally or alternatively, the electrodes 112 of each lead 110 may be configured separately to emit excitation pulses.

FIGS. 2A-2I, respectively, depict stimulation portions 200-208 for inclusion at the distal end of lead. For example, the stimulation portions 200-208 depict a conventional stimulation portion of a "percutaneous" lead with multiple electrodes 112. The stimulation portions 200-208 depict a stimulation portion including several segmented electrodes 112. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portions 204-208 include multiple electrodes 112 on alternative paddle structures than shown in FIG. 1.

In connection to FIG. 1, the lead 110 may comprise a lead body 172 of insulative material about a plurality of conductors within the material that extend from a proximal end of lead 110, proximate to the IPG 150, to its distal end. The conductors electrically couple a plurality of the electrodes 112 to a plurality of terminals (not shown) of the lead 110. The terminals are adapted to receive electrical pulses and the electrodes 112 are adapted to apply the pulses to the stimulation target of the patient. It should be noted that although the lead 110 is depicted with twenty electrodes 112, the lead 110 may include any suitable number of electrodes 112 (e.g., less than twenty, more than twenty) as well as terminals, and internal conductors.

Although not required for all embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

Figure 3:
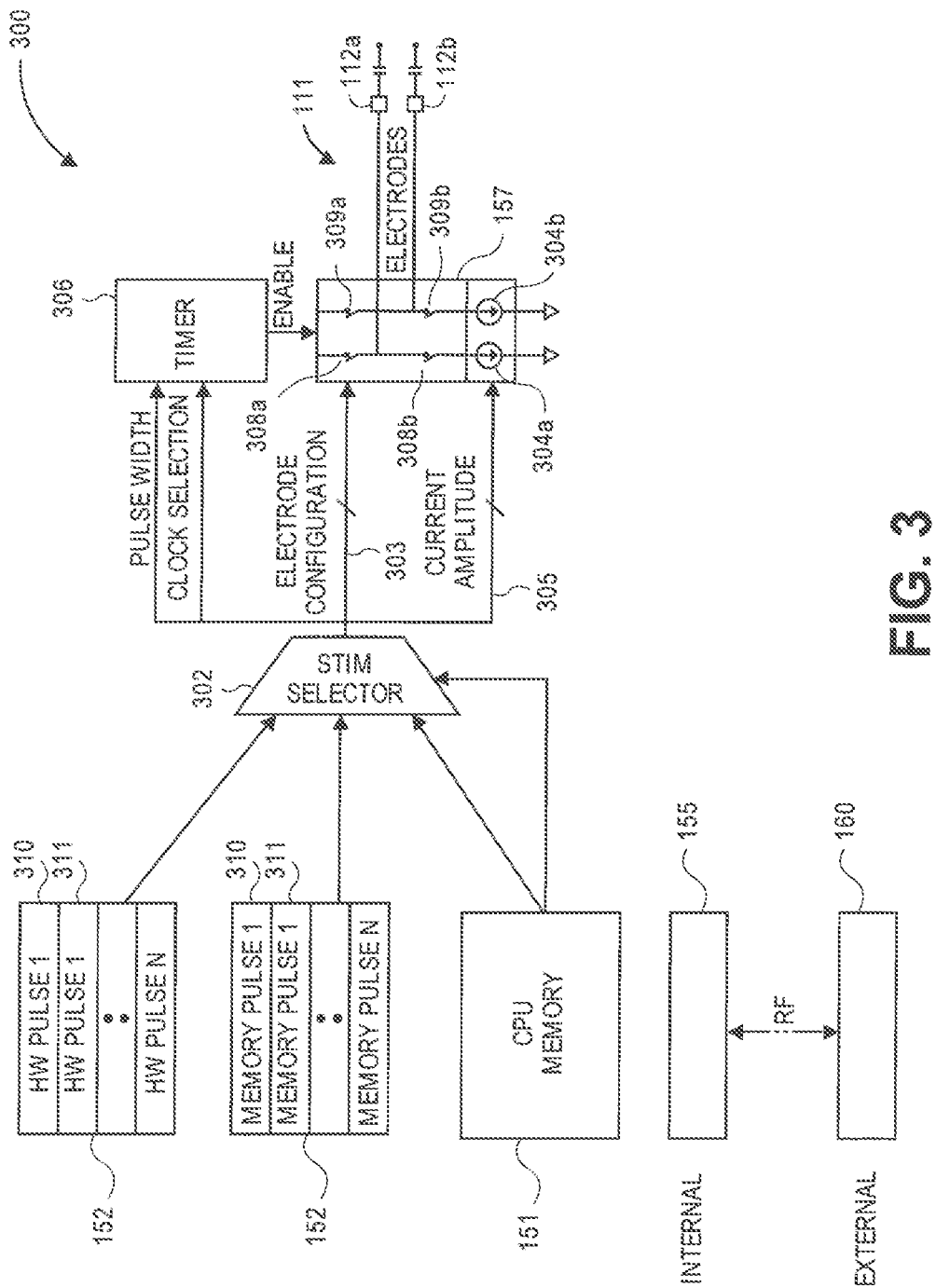
FIG. 3 depicts a schematic block diagram of an embodiment of first, second, and third generator circuits within the neurostimulation device shown in FIG. 1.

FIG. 3 depicts a schematic block diagram 300 of the first, second, and third generator circuits 152, 163, 151 within the NS device 100. The first, second, and third generator circuits 152, 163, 151 are operably coupled to a multiplexer 302. The multiplexer 302 is configured to operably couple one of the first, second, and third generator circuits 152, 163, 151 to the switching circuitry 157, a timer circuit 306, and electrical source circuits 304a-b.

The multiplexer 302 is operably coupled via a bus 303 to an array of switches 308a-b, 309a-b representing the switching circuitry 157. The bus 303 is electrically coupled to each of the array of switches 308a-b, 309a-b of the switching circuitry 157. For example, the bus 303 enables the first, second, and third generator circuits 152, 163, 151 to activate individual switches of the array of switches 308a-b, 309a-b. The array of switches are shown in an "H-bridge" configuration. The array of switches 308a-b, 309a-b activate the electrodes 112a-b, and configure the electrodes 112a-b as an anode or cathode.

The array of switches 308a-b, 309a-b are operably coupled to corresponding electrical source circuits 304a-b and a timer circuit 306. The electrical source circuits 304a-b can represent current and/or voltage sources. The electrical source circuits 304a-b provide current and/or voltage to the electrodes 112a-b. An amount of current and/or voltage generated by the electrical source circuits 304a-b is based on instructions received by the first, second, and third generator circuits 152, 163, 151. For example, an amount of current generated by the electrical source circuit 304a-b is based on an amplitude instruction received from the first, second, or third generator circuits 152, 163, 151. The amplitude instruction is received along a bus 305 to each of the electrical source circuits 304a-b. For example, the bus 305 enables the first, second, and third generator circuits 152, 163, 151 to adjust the electrical source circuits 304a-b individual).

The timer circuit 306 is configured to limit a duration of time for the activation of the array of switches 308a-b, 309a-b. The timer circuit 306 receives instructions from the first, second, or third generator circuits 152, 163, 151 to define a pulse width and/or a dock selection. The timer circuit 306 transmits an enable signal for the switching circuitry 157 that defines an activation length of the array of switches 308a-b, 309a-b.

For example, the first generator circuit 152 is a hardware-based circuit that output state signals that direct operation of the array of switches 308a-b, 309a-b, an amplitude instruction for the electrical source circuits 304a-b, and a pulse width instruction for the timer circuit 306. The first generator circuit 152 activates the switches 308a and 309b to open and/or close states. For example, the first generator circuit 152 may set the electrical source circuit 304h to provide a current of 10 mA. For example, the electrode 112b is configured as an anode and the electrode 112a is configured as a cathode providing a 10 mA pulse for the NS therapy. For example, the first generator circuit 152 may instruct the timer circuit 306 to have a pulse width of 30 microseconds. For example, the time circuit 306 transmits enable signals to the switching circuitry 157 that define pulses having the 10 mA amplitude and 30 microseconds pulse width.

The first generator circuit 152 is configured as a dedicated stimulation waveform generator. For example, the first generator circuit 152 includes one or more counters, comparators, and/or the like. The counters and comparators are configured to activate the individual switches of the array of switches 308a-b, 309a-b based on counter values.

The first generator circuit 152 is configured to generate the first type of stimulation waveform. The first type of stimulation waveform includes rectangular pulses of varying pulse widths and frequencies. Optionally, the rectangular pulses may be generated with different amplitudes up to a maximum amplitude defined by a supported amplitude. The amplitude of the rectangular pulses of the first type of stimulation waveform is limited by the supported amplitude. The pulse width and frequency of the rectangular pulses are limited by the clock timing resolution of the clock of the first generator circuit 152. The clock timing resolution represents a frequency of an operating clock (e.g., an oscillator) of the first generator circuit 152. Optionally, the clock timing resolution represents a maximum frequency of the one or more counters of the first generator circuit 152. For example, when the frequency of the clock is limited to 100 kHz, the frequency of the rectangular pulses is limited to 100 kHz, and a minimum pulse width of the rectangular pulses is no less than 10 microseconds.

The first generator circuit 152 transmits instructions 310-311 to the multiplexer 302 to form a target stimulation waveform. Each instruction 310-311 defines a segment of the target stimulation waveform. Based on the instructions 310-311, the rectangular pulses of the target stimulation waveform are defined. For example, the instruction 310 defines a pulse width, a target amplitude resolution, and electrode configuration to form a pulse of the target stimulation waveform. For example, the first generator circuit 152 transmits the instruction 310 to the multiplexer 302, corresponding to a first segment. The instruction 310 includes a pulse width of 30 microseconds, an amplitude of 10 mA, with an electrode configuration of the electrode 112a as an anode and the electrode 112b as a cathode. The multiplexer 302 partitions the instruction 310 to the corresponding timer circuit 306, the switching circuitry 157, and the electrical source circuits 304a-b. The instructions 310-311 can represent hardware register configurations that adjust hardware circuits of the first generator circuit 152 to generate the target stimulation waveforms. For example, the first generator circuit 152 can customize the first type of stimulation waveform based on the clock timing resolution and the supported amplitude to form the target stimulation waveform.

Additionally or alternatively, an example and discussion of "constant current" pulse generating circuitry (e.g., first generator circuit 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein, by reference. One or multiple sets of such circuitry may be provided within the IPG 150. Different pulses on different electrodes 112 may be generated using a single set of the first generator circuit 152 using consecutively generated pulses according to a "multi-stimset program" as is known in the art. Complex stimulation parameters may be employed such as those described in U.S. Pat. No. 7,228,179, entitled "Method and apparatus for providing complex tissue stimulation patterns," and International Patent Publication Number WO 2001/093953 A1 entitled "NEUROMODULATION THERAPY SYSTEM," which are expressly incorporated herein by reference. Alternatively, multiple sets of such circuitry may be employed to provide pulse patterns (e.g., the tonic stimulation waveform, the burst stimulation waveform) that include generated and delivered stimulation pulses through various electrodes 112 of the one or more leads 110 as is also known in the art. Various sets of stimulation parameters may define the characteristics and timing for the pulses applied to the various electrodes 112 as is known in the art. Although constant excitation pulse generating circuitry is contemplated for some embodiments, any other suitable type of pulse generating circuitry may be employed such as constant voltage pulse generating circuitry.

The second generator circuit 163 is a DMA based circuit that is configured to store instructions 320-321 in a tangible and non-transitory memory. The second generator circuit 163 represents direct memory access that includes the instructions 320-321, which form the target stimulation waveform.

The second generator circuit 163 is configured to generate the second type of stimulation waveform. The second type of stimulation waveforms represent complex rectangular and non-rectangular pulses with varying pulse widths and frequencies that are not readily described with a mathematical relationship between the pulses therein. Non-limiting examples of the non-rectangular pulses are triangle pulses, sawtooth pulses, and/or the like. The second type of stimulation waveform can include amplitude resolutions that are not limited by a supported amplitude of the second generator circuit 163. For example, the amplitude resolutions of stimulation waveforms generated by the second generator circuit 163 is not limited by a supported amplitude as the first generator circuit 152. The second generator circuit 163 transmits instructions 320-321 to the multiplexer 302 to form the target stimulation waveform. Each instruction 320-321 defines a segment of the target stimulation waveform. Based on the instructions 320-321, the target stimulation waveform is generated by the second generator circuit 163. For example, the instruction 320 defines a pulse width and clock selection for the timer circuit 306, an electrode configuration for the switching circuitry 157, and an amplitude for the electrical source circuits 304a-b. For example, the second generator circuit 163 transmits the instruction 320 to the multiplexer 302. The instruction 320 includes a pulse width of 5 microseconds, an amplitude of 25 mA, with an electrode configuration of the electrode 112a as an anode and the electrode 112b as a cathode. The multiplexer 302 partitions the instruction 320 to the corresponding timer circuit 306, the switching circuitry 157, and the electrical source circuits 304a-b. The instructions 320-321 activate individual switches of the array of switches 308a-b, 309a-b based on the target stimulation waveform.

The clock selection defines a dock frequency with a corresponding clock timing resolution generated by the timer circuit 306. The clock selection is utilized to define a minimum pulse width and/or frequency of the second type of stimulation waveform. For example, the clock timing resolution of 500 kHz enables a pulse width of no less than two microseconds for the target stimulation waveform. It may be noted that the timer circuit 306 includes a plurality of clock timing circuits. The clock timing circuits include different frequency values, which can be selected by the second generator circuit 163. For example, the clock timing circuit includes frequency values that can be greater than the clock timing resolution of the clock of the first generator circuit 152. The selection of the clock timing circuits of the timer circuit enable the second generator circuit 163 to generate the second type of stimulation waveforms that have smaller pulse widths and/or frequencies relative to the first type of stimulation waveform.

An amount of memory utilized by the second generator circuit 163 is based on the timing resolution of the target stimulation waveform. The second generator circuit 163 requires instructions 320-321 for each change in amplitude, pulse width, frequency, and/or electrode configuration. For example, the second generator circuit 163 includes instructions 320-321 for the target stimulation waveform. The electrode configuration of the target stimulation waveform has the electrode 112b as an anode and the electrode 112 as the cathode. The target stimulation waveform includes a slope increasing an amplitude from 2 mA to 10 mA in 10 microseconds. The instructions 320-321 include adjusting the current generated by the electrical source circuits 304a-b by 0.8 mA every 1 microsecond. The timing resolution of the slope requires a change every 1 microsecond, which requires instructions 320-321 stored in the memory to adjust the current generated by the electrical source circuits 304a-b. The instructions 320-321 are transmitted to the multiplexer 302, which partitions the instructions 320-321 to the clock circuit 306, the switching circuitry 157, and the electrical source circuits 304a-b. The instruction 320 includes a clock selection of 1000 kHz and a pulse width of 1 microsecond. The switching circuitry 157 activates the switch 308a and 309b to configure the electrode 112b as the anode and the electrode 112b as the cathode. The electrical source circuit 304b is adjusted to generate the current to 2 mA. The instruction 321 is similar to the instruction 320, but includes instructions to adjust the current generated by the electrical source circuit 304b to 2.8 mA. The subsequent instructions continually increase the current generated by the electrical source circuit 304b by 0.8 mA every 1 microsecond until the 10 mA is reached.

The third generating circuit 151 may include one or more processors, a central processing unit (CPU), one or more microprocessors, or any other electronic component capable of processing input data according to program instructions. Optionally, the third generating circuit 151 may include and/or represent one or more hardware circuits or circuitry that include, are connected with, or that both include and are connected with one or more processors, controllers, and/or other hardware logic-based devices. Additionally or alternatively, the third generator circuit 151 may execute instructions stored on a tangible and non-transitory computer readable medium (e.g., the memory 161, integrated with the third generating circuit 151). A minimum pulse width and/or frequency of the third type of stimulation waveform is limited based on a processing power and/or frequency of the third generating circuit 151. The third generating circuit 151 may be configured to control the operation of the NS device 100. The instructions defines segments of the target stimulation waveform, which are sent to the multiplexer 302. For example, the instructions activate individual switches of the array of switches 308a-b, 309a-b based on the target stimulation waveform. The third generator circuit 151 transmits the instructions to the multiplexer 302 to form the target stimulation waveform.

The third generator circuit 151 generates the third type of stimulation waveform. The third type of stimulation waveforms represent rectangular and non-rectangular pulses having a mathematical relationship between the target amplitude resolutions of the pulses. The mathematical relationship can be based on an algorithm stored in the tangible and non-transitory computer readable medium of the third generator circuit 151. Non-limiting examples of a mathematical relationship includes a sinusoidal relationship (e.g., oscillation) of the target amplitude resolutions, pseudo-random target amplitude resolutions overtime, a dependency of the target amplitude resolutions, an exponential relationship of the target amplitude resolutions, a parabolic relationship of the target amplitude resolutions, and/or the like.

Figure 4:
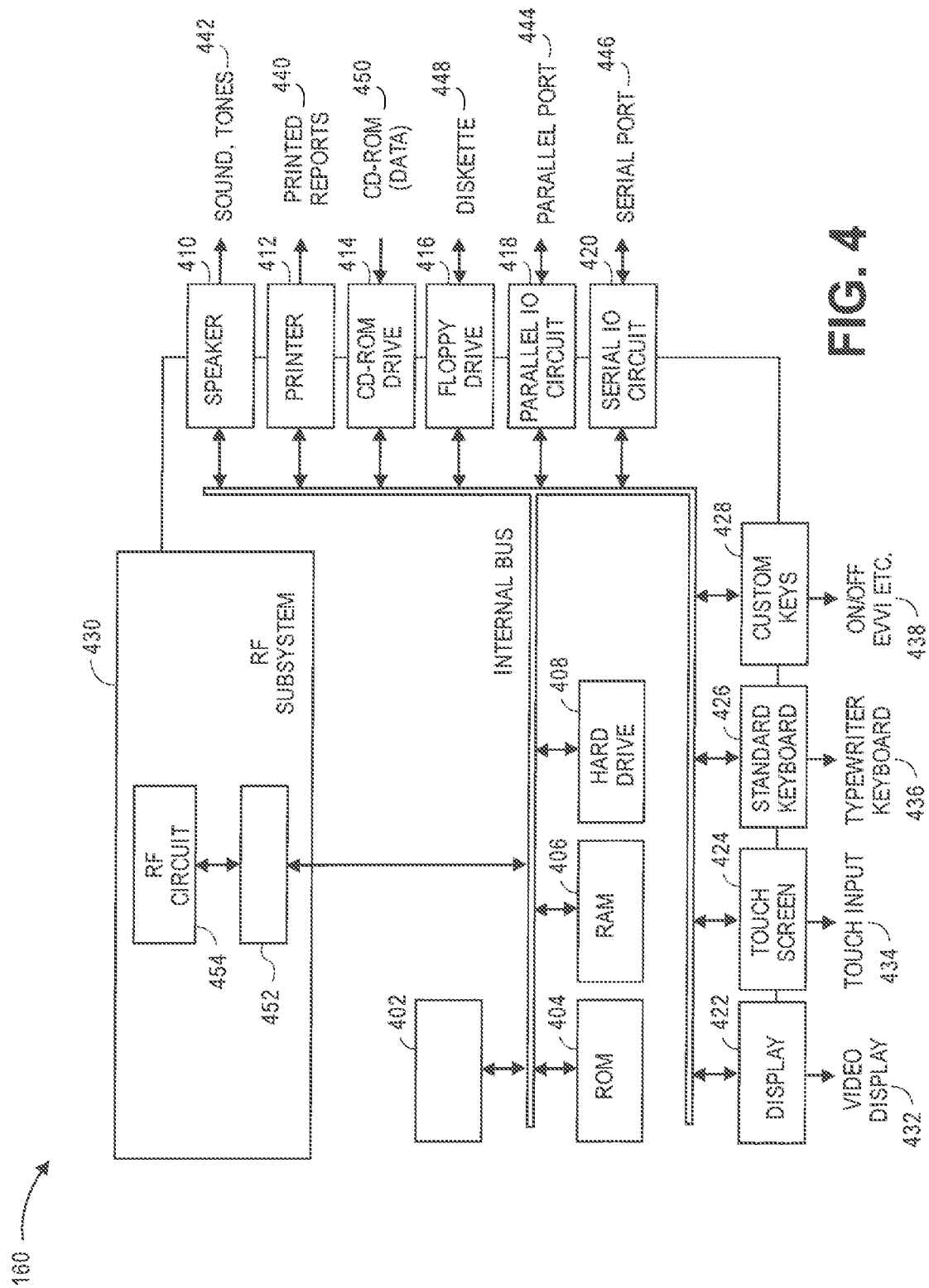
FIG. 4 depicts a schematic block diagram of an embodiment of an external device.

The external device 160 may be implemented to charge/recharge the battery 154 of the IPG 150 (although a separate recharging device could alternatively be employed), to access the memory 161, and to program the IPG 150 on the pulse specifications while implanted within the patient. FIG. 4 depicts a schematic block diagram of an embodiment of the external device 160. The external device 160 may be a workstation, a portable computer, an NS system programmer, a PDA, a cell phone, a smart phone, a tablet, and/or the like.

The external device 160 includes an internal bus that connects/interfaces with a Central Processing Unit (CPU) 402, ROM 404, RAM 406, a hard drive 408, a speaker 410, a printer 412, a CD-ROM drive 414, a floppy drive 416, a parallel I/O circuit 418, a serial I/O circuit 420, a display 422, a touch screen 424, a standard keyboard 426, custom keys 428, and a radio frequency (RF) subsystem 430. The internal bus is an address/data bus that transfers information between the various components described herein. The hard drive 408 may store operational programs as well as data, such as waveform templates and detection thresholds.

The controller circuit 402 is configured to control the operation of the external device 160. The controller circuit 402 may include one or more processors. Optionally, the controller circuit 402 may include one or more processors, one or more microprocessors, a graphics processing unit (GPU), or any other electronic component capable of processing inputted data according to specific logical instructions. Optionally, the controller circuit 402 may include and/or represent one or more hardware circuits or circuitry that include, are connected with, or that both include and are connected with one or more processors, controllers, and/or other hardware logic-based devices. Additionally or alternatively, the controller circuit 402 may execute instructions stored on a tangible and non-transitory computer readable medium (e.g., the ROM 404, the RAM 406, hard drive 408).

Optionally, the controller circuit 402 may include RAM or ROM memory, logic and timing circuitry, state machine circuitry, and/or I/O circuitry to interface with the NS device 100. The display 422 may be connected to a video display 432. The touch screen 424 may display graphic information relating to the NS device 100. The display 422 displays various information related to the processes described herein.

The touch screen 424 accepts a user's touch input 434 when selections are made. The keyboard 426 (e.g., a typewriter keyboard 436) allows the user to enter data to the displayed fields, as well as interface with the RF subsystem 430. The touch screen 424 and/or the keyboard 426 is configured to allow the user to operate the NS device 100. The external device 160 may be controlled by the user (e.g., doctor, clinician, patient) through the touch screen 424 and/or the keyboard 426 allowing the user to interact with the NS device 100. The touch screen 424 and/or the keyboard 426 may permit the user to move electrical stimulation along and/or across one or more of the lead(s) 110 using different electrode 112 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. Optionally, the touch screen 424 and/or the keyboard 426 may permit the user to designate which electrodes 112 are to stimulate (e.g., emit excitation pulses, in an anode state, in a cathode state) the stimulation target.

Custom keys 428 turn on/off 438 the external device 160. The printer 412 prints copies of reports 440 for a physician to review or to be placed in a patient file, and the speaker 410 provides an audible warning (e.g., sounds and tones 442) to the clinician and/or patient. The parallel I/O circuit 418 interfaces with a parallel port 444. The serial I/O circuit 420 interfaces with a serial port 446. The floppy drive 416 accepts diskettes 448. Optionally, the floppy drive 416 may include a USB port or other interface capable of communicating with a USE device such as a memory stick. The CD-ROM drive 414 accepts CD ROMs 450.

The RF subsystem 430 includes a central processing unit (CPU) 452 in electrical communication with an RE circuit 454. The RE subsystem 430 is configured to receive and/or transmit information with the NS device 100. The RE subsystem 430 may represent hardware that is used to transmit and/or receive data along a urn-directional and/or bi-directional communication link. The RF subsystem 430 may represent a communication circuit. For example, the RF subsystem 430 includes a transceiver, receiver, transceiver and/or the like and associated circuitry (e.g., antennas) for wirelessly communicating (e.g., transmitting and/or receiving) with the NS device 100. For example, protocol firmware for transmitting and/or receiving data along the uni-directional and/or bi-directional communication link may be stored in the memory (e.g., the ROM 404, the RAM 406, the hard drive 408), which is accessed by the CPU 452. The protocol firmware provides the network protocol syntax for the CPU 452 to assemble data packets, establish and/or partition data received along the uni-directional and/or bi-directional communication links, and/or the like. The uni-directional and/or bi-directional communication link can represent a wireless communication (e.g., utilizing radio frequency (RE)) link for exchanging data (e.g., data packets) between the NS device 100 and the external device 160. The uni-directional and/or bi-directional communication link may be based on a customized communication protocol and/or a standard communication protocol, such as Bluetooth, NFC, RFID, GSM, infrared wireless LANs, HIPERLAN, 3G, LTE, and/or the like.

Additionally or alternatively, the RF subsystem 430 may be operably coupled to a "wand" 165 (FIG. 1). The wand 165 may be electrically connected to a telemetry component 166 (e.g., inductor coil, RE transceiver) at the distal end of wand 165 through respective wires (not shown) allowing bi-directional communication with the NS system 100. For example, the user may initiate communication with the NS system 100 by placing the wand 165 proximate to the NS system 100. Preferably, the placement of the wand 165 allows the telemetry system of the wand 165 to be aligned with the communication circuit 155.

Also, the external device 160 may permit operation of the IPG 150 according to one or more NS programs or therapies to treat the patient. For example, the NS program corresponds to the NS therapy and/or executed by the IPG 150. Each NS program may include one or more sets of stimulation parameters of the pulses including pulse amplitude, stimulation level, pulse width, pulse frequency or inter-pulse period, pulse repetition parameter (e.g., number of times for a given pulse to be repeated for respective stimset during execution of program), biphasic pulses, monophasic pulses, etc. The IPG 150 may modify its internal parameters in response to the control signals from the external device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 5:
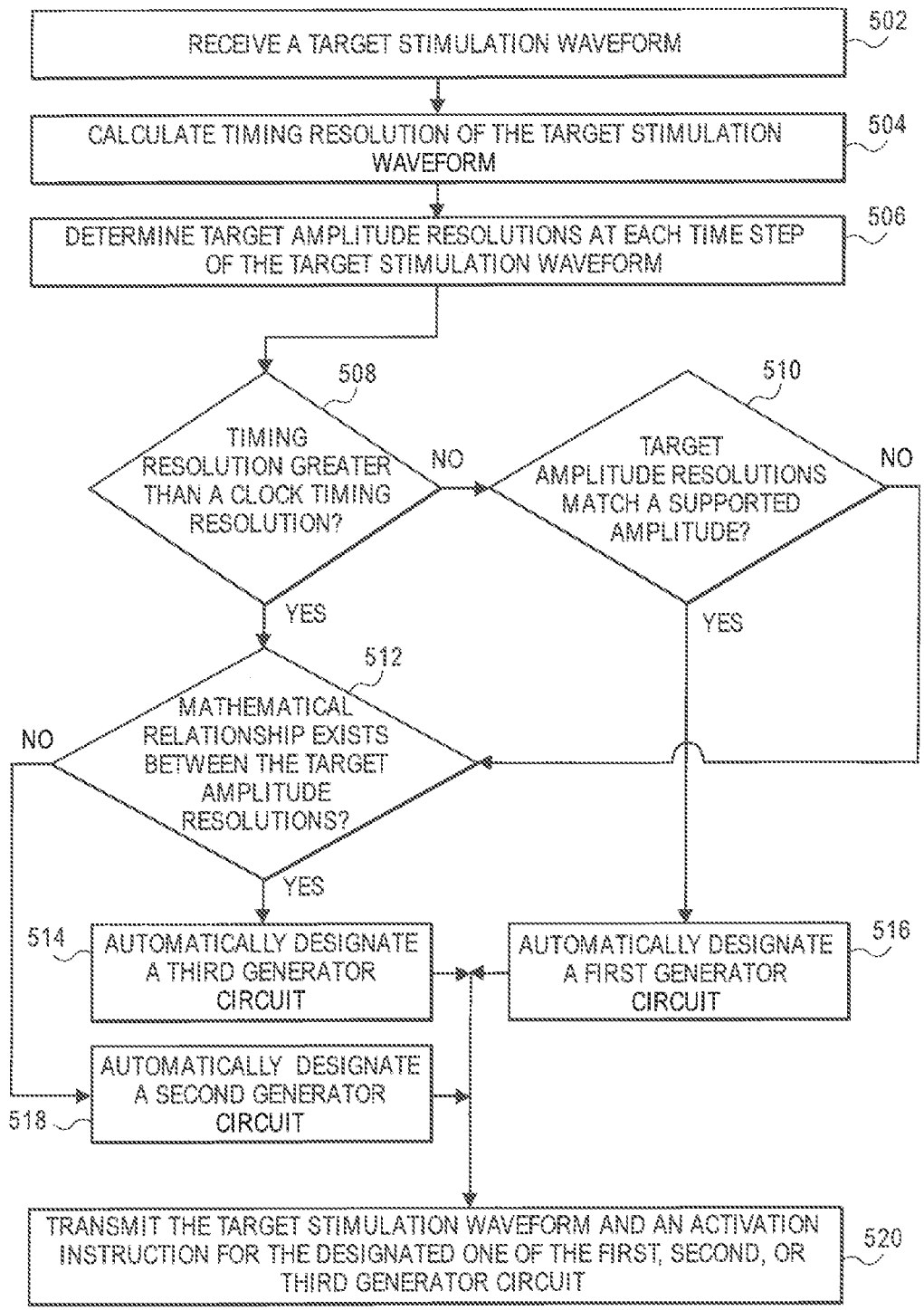
FIG. 5 illustrates a flowchart of an embodiment of a method for generating a stimulation waveform for a neurostimulation therapy.

In connection with FIG. 5, the external device 160 is configured to receive a target stimulation waveform from the clinician. Based on characteristics of the target stimulation waveform, the external device 160 automatically designate the first, second, or third generator circuits 151, 163, 152 to generate the target simulation waveform in the NS device 100.

FIG. 5 illustrates a flowchart of an embodiment of a method 500 for electrode monitoring. The method 500, for example, may employ structures or aspects of various embodiments systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 501) may be used as one or more algorithms to direct hardware to perform one or more operations described herein.

Beginning at 502, the external device 160 receives a target stimulation waveform 602. FIG. 6 is a graphical illustration 600 of an embodiment of the target stimulation waveform 602. A user interface of the external device 160 is configured to receive a user input indicative of the target stimulation waveform 602. For example, the clinician may input the target stimulation waveform 602 as a touch input 434 from the touch screen 424, from the standard keyboard 426, and/or the custom keys 428. Additionally or alternatively, the target stimulation waveform 602 may be stored in the memory (e.g., ROM 404, RAM 406, hard drive 408) of the external device 160 and selected by the clinician using the user interface (e.g., touch screen 424, standard keyboard 426, custom keys 428).

At 504, the controller circuit 402 calculates a timing resolution 604 of the target stimulation waveform 602. The timing resolution 604 can represent a frequency of the target stimulation waveform 602. For example, the timing resolution 604 is indicative of the periodic relationship of pulses 612-613 of the target stimulation waveform 602 over time. Based on a rate of the periodic relationship repeats, the controller circuit 402 identifies the timing resolution 604. For example, the controller circuit 402 calculates the timing resolution 604 as 50 kHz.

Additionally or alternatively, a timing resolution represents a minimum pulse width 610 of the target stimulation waveform 602. For example, the controller circuit 402 identifies a portion of the target stimulation waveform 602 representing a transition between target amplitude resolutions 606, 608. The controller circuit 402 compares the identified portions of the target stimulation waveform 602 with each other to identify the shortest transition time. The minimum pulse width 610 is identified by the controller circuit 402 as the shortest transition of the target stimulation waveform 602. For example, the controller circuit 402 identified the minimum pulse width 610 as 20 microseconds representing the timing resolution 604 of 50 kHz.

At 506, the controller circuit 402 determines the target amplitude resolutions 606, 608 at each time step of the target stimulation waveform 602 over time. The time steps represent the target amplitude resolutions 606, 608 of the pulses 612-613 of the target stimulation waveform 602. The target amplitude resolutions 606, 608 represent peak amplitudes, a pulse width, a shape of the pulses 612-613, and/or the like. For example, the shape of the pulses 612-613 may be represent a rectangular pulse, a non-rectangular pulse, and/or the like. The controller circuit 402 determines the target amplitude resolutions 606, 608 of the target stimulation waveform 602. For example, the controller circuit 402 determines a morphology of the pulses 612-613, amplitude peaks of the pulses 612-613, and/or the like. The morphology of the pulses 612-613 may represent a slope of the pulses 612-613, overall shape of the pulses 612-613, and/or the like. The controller circuit 402 determines that the pulses 612-613 represent rectangular pulses based on the slopes of the pulses 612-613. The controller circuit 402 further determines the target amplitude resolutions 606, 608 of the target stimulation waveform 602 includes peak amplitudes of 5 mA. Additionally or alternatively, the target stimulation waveform can include a single target amplitude resolution and/or a single pulse. For example, the target stimulation waveform 602 may include a single target amplitude resolution.

At 508, the controller circuit 402 determines whether the timing resolution 604 is greater than the clock timing resolution of the first generator circuit 152. The controller circuit 402 is configured to compare the timing resolution 604 with the clock timing resolution of the first generator circuit 152. The clock defines a frequency limit of the first type of stimulation waveform that can be generated by the first generator circuit 152. For example, the clock timing resolution of the first generation circuit 152 is 100 kHz. The controller circuit 402 compares the clock timing resolution with the timing resolution 604. The controller circuit 402 determines that the timing resolution 604, 50 kHz, matches the clock timing resolution of 100 kHz. For example, the timing resolution 604 falls within the clock timing resolution of the first generator circuit 152.

If the timing resolution 604 is not greater than the clock timing resolution, then at 510, the controller circuit 402 determines whether the amplitude matches a supported amplitude of the first generator circuit 152. The controller circuit 402 is configured to compare the target amplitude resolutions 606, 608 with the supported amplitude of the first generator circuit 152. The supported amplitude represents the maximum amplitude that can be generated by the first generator circuit 152. For example, the supported amplitude of the first generator circuit 152 is 10 mA. The controller circuit 402 determines that the pulses 612-613 are rectangular pulses and is supported by the first generator circuit 152. Additionally, the controller circuit 402 compares the target amplitude resolutions 606, 608 with the supported amplitude of the first generator circuit 152. The controller circuit 402 determines that the target amplitude resolutions 606, 608, 5 mA, matches the supported amplitude of 10 mA. For example, the target amplitude resolutions 606, 608 falls within the supported amplitude of the first generator circuit 152.

If the amplitude matches the supported amplitude, then at 516, the controller circuit 402 automatically designates the first generator circuit 152. For example, the controller circuit 402 determines that the timing resolution 604 matches the clock timing resolution and the target amplitude resolutions 606, 608 matches the supported amplitude of the first generator circuit 152. Since the degree to which the target stimulation waveform 602 matches the first type of stimulation waveform that can be generated by the first generator circuit 152, the controller circuit 402 automatically designates the first generator circuit 152 to generate the target stimulation waveform 602.

If the timing resolution is greater than the clock timing resolution and/or if the target amplitude resolutions 606, 608 do not match the supported amplitude, then at 512, the controller circuit 402 determines whether a mathematical relationship exists between the target amplitude resolutions 706-713. FIG. 7 is a graphical illustration 700 of an embodiment of a target stimulation waveform 702. The controller circuit 402 calculates a timing resolution 704 of the target stimulation waveform 702. For example, the timing resolution 704 is determined by the controller circuit 402 to be 150 kHz. The clock timing resolution of the first generator circuit 152 is identified by the controller circuit 402 as 100 kHz. The controller circuit 402 compares the timing resolution 704 with the clock timing resolution, and determines the timing resolution 704 is greater than or does not fall within the clock timing resolution.

Additionally or alternatively, the controller circuit 402 compares target amplitude resolutions 706-713 with the supported amplitude of the first generator circuit 152. For example, the supported amplitude of the first generator circuit 152 can be 10 mA. The controller circuit 402 determines a magnitude of the target amplitude resolutions 706-713 of the target stimulation waveform 702. The controller circuit 402 compare the magnitudes of the target amplitude resolutions 706-713 with the supported amplitude. For example, the controller circuit 402 determines the target amplitude resolution 710 is 12 mA. The controller circuit 402 determines that the target amplitude resolution 710 does not match and is greater than the supported amplitude of the first generator circuit 152.

Optionally, the controller circuit 402 may compare a morphology amplitude, shape, slope) of the pulses 715-716 of the target stimulation waveform 702. For example, the first type of stimulation waveform generated by the first generator circuit 152 includes rectangular pulses. The controller circuit 402 identifies a morphology of the target amplitude resolutions 712-713 of the pulses 715-716. For example, the target amplitude resolutions 712-713 have a slope representing a portion of a triangle pulse. The controller circuit 402 determines that the slope does not represent a rectangle pulse, and are not supported by the first generator circuit 152. Based on the slope of the target amplitude resolutions 712-713 of the pulses 715-716, the controller circuit 402 determines the target amplitude resolutions 712-713 do not match the supported amplitude of the first generator circuit 152.

At 512, the controller circuit 402 identifies whether a mathematical relationship exists based on a relationship of the target amplitude resolutions 706-713 of the target stimulation waveform 702. For example, the mathematical relationship is indicative of a mathematical algorithm that describes and/or forms the target amplitude resolutions 706-713 of the target stimulation waveform 702.

For example, the controller circuit 402 compares the target amplitude resolutions 706-713 of the target stimulation waveform 702 with each other to identify the mathematical relationship. The controller circuit 402 determines that the target amplitude resolutions 706-713 do not have a sinusoidal relationship. For example, the target stimulation waveform 702 includes rectangular pulses represented by the target amplitude resolutions 706 and 709, and 710. The controller circuit 402 determines the target amplitude resolutions 706-713 are not pseudo-random. For example, the controller circuit 402 identifies the periodic relationship of the pulses 715, 716 having the target amplitude resolutions 706-713 repeating at the time resolution 704. The controller circuit 402 determines that the target amplitude resolutions 706-713 do not have a dependency. For example, the target amplitude resolutions 706-713 can be dependent on electrical characteristics (e.g., impedance) between the electrodes 112a-b, sensor measurements, and/or the like. Based on the consistency of the target amplitude resolutions 706-713, the controller circuit 402 determines that no dependency of the target amplitude resolutions 706-713 exists. The controller circuit 402 further determines that no exponential and/or parabolic relationship between the target amplitude resolutions 706-713 exists. Based on the above determinations, the controller circuit 402 determines that no mathematical relationship exists between the target amplitude resolutions 706-713.

If no mathematical relationship exists, then at 518, the controller circuit 402 automatically designates the second generator circuit 163. For example, the controller circuit 402 automatically designates the second generator circuit 163 when no mathematical relationship exists and the timing resolution 704 differs from the clock timing resolution for the clock of the first generator circuit 152. Additionally or alternatively, the target amplitude resolutions 706-713 do not match the supported amplitudes of the first generator circuit 152.

Figure 8:
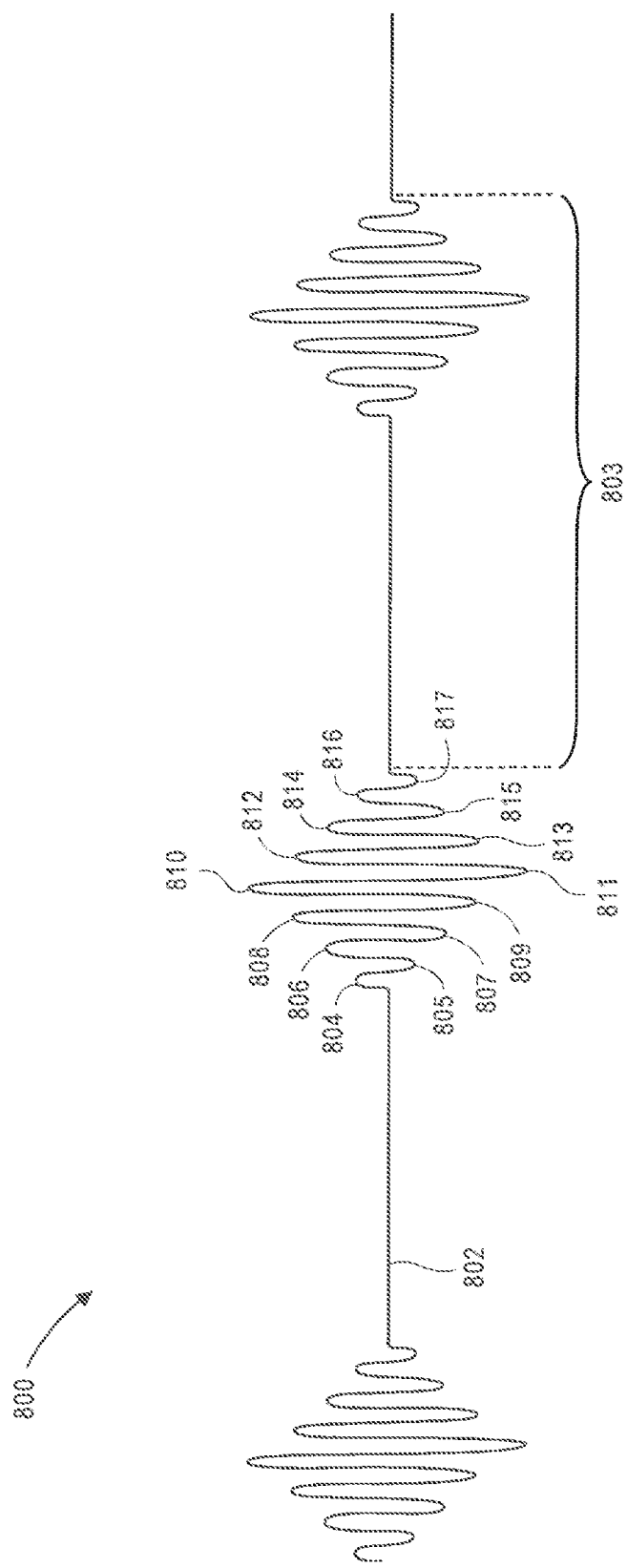
FIG. 8 is a graphical illustration of an embodiment of a target stimulation waveform.

If a mathematical relationship exists, then at 514, the controller circuit 402 automatically designates the third generator circuit 151, FIG. 8 is a graphical illustration 800 of an embodiment of a target stimulation waveform 802. The controller circuit 402 identified a timing resolution 803 of 150 kHz, which does not match the clock timing resolution for the clock of the first generator circuit 152. The controller circuit 402 identifies the mathematical relationship between the target amplitude resolutions 804-817. For example, the controller circuit 402 determines a morphology of the target amplitude resolutions 804-817, amplitude peaks of the target amplitude resolutions 804-817, and/or the like. Based on the morphology, the controller circuit 402 determines the target amplitude resolutions 804-817 have a sinusoidal relationship such that the target amplitude resolutions 804-817 oscillate. The controller circuit 402 is configured to automatically designate the third generator circuit 151 when the mathematical relationship exists.

At 520, the controller circuit 402 transmits the target stimulation waveform 602, 702, 802 and an activation instruction for the designated one of the first, second, or third generator circuit 151, 163, 152.

For example, the controller circuit 402 instructs the RF subsystem 430 to transmit the target stimulation waveform 602 and the activation instruction for the first generator circuit 152 along the communication link to the NS device 100. The target stimulation waveform 602 may include a plurality of instructions that configure the first generator circuit 152. For example, the instructions (e.g., hardware register configurations) configure the counter, comparators, and/or the like of the first generator circuit 152 to form the first type of stimulation waveform to match the target stimulation waveform 602. The instructions include the timing resolution 604 indicating the frequency for the clock timing resolution of the clock of the first generator circuit 152, the target amplitude resolutions 606, 608, and/or the like. The controller circuit 402 further communicates the activation instruction for the first generator circuit 152. The activation instruction includes instructions that the first generator circuit 152 is designated by the controller circuit 402 to generate the target stimulation waveform 602.

Additionally or alternatively, the activation instruction further instructs the second and third generator circuits 163, 151 not designated by the controller circuit 402 to enter a sleep mode or state. The sleep mode represents a low power mode. During the sleep mode components of the first, second, and/or third generator circuits 152, 163, 151 are turned off. For example, the counter, comparator, and/or the like of the first generator circuit 152 is turned off and/or does not receive electrical power from the battery 154. In another example, the tangible non-transitory memory of the second generator circuit 163 does is turned off and/or does not receive electrical power from the battery 154. In another example, the one or more processors of the third generator circuit 151 suspends operations reducing demand of electrical power from the battery 154.

In another example, the controller circuit 402 instructs the RF subsystem 430 to transmit the target stimulation waveform 702 and the activation instruction for the second generator circuit 163 along the communication link to the NS device 100. The target stimulation waveform 702 may include a plurality of instructions that are stored in the tangible non-transitory memory of the second generator circuit 163. For example, the instructions represent characteristics of the target stimulation waveform 702. The instructions include the timing resolution 704 indicating the frequency for the clock selection of the timer circuit 306, the target amplitude resolutions 706-713, and/or the like. The controller circuit 402 further communicates the activation instruction for the second generator circuit 163. The activation instruction includes instructions that the second generator circuit 163 is designated by the controller circuit 402 to generate the target stimulation waveform 702, and that the first and third generator circuits 152, 151 enter the sleep mode.

In another example, the controller circuit 402 instructs the RF subsystem 430 to transmit the target stimulation waveform 802 and the activation instruction for the third generator circuit 151 along the communication link to the NS device 100. The target stimulation waveform 802 may include a plurality of instructions that are stored in the tangible non-transitory memory of the third generator circuit 151. The plurality of instructions are executed by the one or more processors of the third generator circuit 151. For example, the instructions are generated by the controller circuit 402 as a mathematical algorithm representing the target stimulation waveform 802. The instructions include the timing resolution 804 indicating the frequency, the target amplitude resolutions 804-817, the mathematical relationship between the target amplitude resolutions 804-817 (e.g., sinusoidal relationship), and/or the like. The controller circuit 402 further communicates the activation instruction for the third generator circuit 151. The activation instruction includes instructions that the third generator circuit 151 is designated by the controller circuit 402 to generate the target stimulation waveform 802, and that the first and second generator circuits 152, 163 enter the sleep mode.

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A system for generating a stimulation waveform for a neurostimulation therapy, the system comprising:
a user interface configured to receive a user input indicative of a target stimulation waveform;
a radio frequency (RF) subsystem configured to establish a communication link with a neurostimulation (NS) device that includes first, second, and third generator circuits configured to generate different first, second, and third types of stimulation waveforms, respectively;
a controller circuit operably coupled to the user interface and the RF subsystem, the controller circuit is configured to:
calculate a timing resolution of the target stimulation waveform;
determine target amplitude resolutions of the target stimulation waveform;
identify whether a mathematical relationship exists between the target amplitude resolutions;
automatically designate one of the first, second, or third generator circuits based on at least one of the timing resolution, the target amplitude resolutions, or the mathematical relationship, wherein the first generator circuit generates electrical pulses of a fixed shape, the second generator circuit generates electrical pulses controlled by amplitude parameters retrieved using dynamic memory access (DMA) operations during pulse generation, and the third generator circuit produces an electrical waveform with non-linear or sinusoidal amplitude variations; and
transmit the target stimulation waveform and an activation instruction for the designated one of the first, second, or third generator circuits along the communication link, wherein the activation instruction activates the first generator circuit that includes a counter and a comparator configured to activate individual switches of an array of switches to generate the target stimulation waveform.

2. The system of claim 1, wherein the controller circuit is configured to compare the timing resolution with a clock timing resolution for a clock of the first generator circuit, the clock timing resolution defining a frequency limit of the first type of stimulation waveform, wherein the controller circuit automatically selects the first generator circuit when the timing resolution fails within the clock timing resolution.

3. The system of claim 1, wherein the controller circuit is configured to compare the target amplitude resolutions with a supported amplitude of the first generator circuit, wherein the controller circuit automatically designates the first generator circuit when the target amplitude resolutions fall within the supported amplitude.

4. The system of claim 1, wherein the controller circuit is configured to automatically designate the second generator circuit when no mathematical relationship exists between the target amplitude resolutions and the timing resolution differs from a clock timing resolution for a clock of the first generator circuit.

5. A system for generating a stimulation waveform for a neurostimulation therapy, the system comprising:
a user interface configured to receive a user input indicative of a target stimulation waveform;
a radio frequency (RF) subsystem configured to establish a communication link with a neurostimulation (NS) device that includes first, second, and third generator circuits configured to generate different first, second, and third types of stimulation waveforms, respectively;
a controller circuit operably coupled to the user interface and the RF subsystem, the controller circuit is configured to:
calculate a timing resolution of the target stimulation waveform;
determine target amplitude resolutions of the target stimulation waveform;
identify whether a mathematical relationship exists between the target amplitude resolutions;
automatically designate one of the first, second, or third generator circuits based on at least one of the timing resolution, the target amplitude resolutions, or the mathematical relationship, wherein the first generator circuit generates electrical pulses of a fixed shape, the second generator circuit generates electrical pulses controlled by amplitude parameters retrieved using dynamic memory access (DMA) operations during pulse generation, and the third generator circuit produces an electrical waveform with non-linear or sinusoidal amplitude variations; and
transmit the target stimulation waveform and an activation instruction for the designated one of the first, second, or third generator circuits along the communication link, wherein the activation instruction activates the second generator circuit that includes a tangible and non-transitory memory that is configured to activate individual switches of an array of switches to generate the target stimulation waveform.

6. A system for generating a stimulation waveform for a neurostimulation therapy, the system comprising:
a user interface configured to receive a user input indicative of a target stimulation waveform;
a radio frequency (RF) subsystem configured to establish a communication link with a neurostimulation (NS) device that includes first, second, and third generator circuits configured to generate different first, second, and third types of stimulation waveforms, respectively;
a controller circuit operably coupled to the user interface and the RF subsystem, the controller circuit is configured to:
calculate a timing resolution of the target stimulation waveform;
determine target amplitude resolutions of the target stimulation waveform;
identify whether a mathematical relationship exists between the target amplitude resolutions;

automatically designate one of the first, second, or third generator circuits based on at least one of the timing resolution, the target amplitude resolutions, or the mathematical relationship, wherein the first generator circuit generates electrical pulses of a fixed shape, the second generator circuit generates electrical pulses controlled by amplitude parameters retrieved using dynamic memory access (DMA) operations during pulse generation, and the third generator circuit produces an electrical waveform with non-linear or sinusoidal amplitude variations; and transmit the target stimulation waveform and an activation instruction for the designated one of the first, second, or third generator circuits along the communication link, wherein the activation instruction activates the third generator circuit that includes one or more processors configured to execute programmed instructions stored on a tangible and non-transitory memory configured to activate individual switches of an array of switches to generate the target stimulation waveform.

7. The system of claim 6, wherein the controller circuit is configured to automatically designate the third generator circuit when the mathematical relationship exists.

* * * * *